United States Patent
Dahmen et al.

(10) Patent No.: US 8,440,852 B2
(45) Date of Patent: *May 14, 2013

(54) METHOD FOR PRODUCING TETRAETHYLENEPENTAMINE

(75) Inventors: Kirsten Dahmen, Freinsheim (DE); Alfred Oftring, Bad Dürkheim (DE); Randolf Hugo, Dirmstein (DE); Thilo Hahn, Kirchheimbolanden (DE); Katrin Baumann, Mannheim (DE); Johann-Peter Melder, Böhl-Iggelheim (DE)

(73) Assignee: BASF SE (DE)

( * ) Notice: Subject to any disclaimer, the term of this patent is extended or adjusted under 35 U.S.C. 154(b) by 370 days.

This patent is subject to a terminal disclaimer.

(21) Appl. No.: 12/529,047

(22) PCT Filed: Feb. 27, 2008

(86) PCT No.: PCT/EP2008/052335

§ 371 (c)(1),
(2), (4) Date: Aug. 28, 2009

(87) PCT Pub. No.: WO2008/104551

PCT Pub. Date: Sep. 4, 2008

(65) Prior Publication Data

US 2010/0029976 A1  Feb. 4, 2010

(30) Foreign Application Priority Data

Mar. 1, 2007 (EP) .................................... 07103292

(51) Int. Cl.
| C07C 209/48 | (2006.01) |
| C07C 253/08 | (2006.01) |
| C07C 211/14 | (2006.01) |
| C07C 255/03 | (2006.01) |
| C07C 255/04 | (2006.01) |

(52) U.S. Cl.
USPC ........... 558/315; 558/351; 558/452; 558/455; 564/491; 564/512

(58) Field of Classification Search ........................ None
See application file for complete search history.

(56) References Cited

U.S. PATENT DOCUMENTS

| 2,769,841 A | 11/1956 | Dylewski et al. |
| 4,146,560 A | 3/1979 | Larkin et al. |
| 4,235,821 A | 11/1980 | Butte, Jr. et al. |
| 4,404,167 A * | 9/1983 | Rozenfeld et al. .............. 422/12 |
| 5,030,740 A | 7/1991 | Bowman et al. |
| 5,530,127 A | 6/1996 | Reif et al. |
| 6,297,394 B1 | 10/2001 | Voit et al. |
| 6,469,211 B2 | 10/2002 | Ansmann et al. |
| 6,518,449 B1 | 2/2003 | Boschat et al. |
| 6,852,669 B2 | 2/2005 | Voit et al. |
| 7,091,153 B2 | 8/2006 | Voit et al. |
| 2006/0041170 A1 | 2/2006 | Jonas et al. |

FOREIGN PATENT DOCUMENTS

| DE | 2755687 A1 | 8/1978 |
| DE | 3003729 A1 | 8/1980 |
| DE | 68911508 T2 | 3/1994 |
| EP | 0212986 A1 | 3/1987 |
| EP | 0222934 A1 | 5/1987 |
| EP | 0382508 A2 | 8/1990 |
| EP | 0696572 A1 | 2/1996 |
| EP | 0913388 A1 | 5/1999 |
| EP | 0963975 A1 | 12/1999 |
| EP | 1209146 A1 | 5/2002 |
| EP | 1742045 A1 | 1/2007 |
| WO | WO-9933561 A1 | 7/1999 |
| WO | WO-99/44984 | 9/1999 |
| WO | WO-2006/071663 A1 | 7/2006 |

OTHER PUBLICATIONS

Nishimura, Shigeo, "Handbook of Heterogeneous Catalytic Hydrogenation for Organic Synthesis", (2001) pp. 213-215.
Malveda, Michael P., "CEH Product Review: Ethyleneamines"; SRI Report, SRI International, (2003), pp. 1-53.
Gamage, Swarna A., et al., "Dicationic Bis(9-methylphenazine-1-carboxamides): Relationships between Biological Activity and Linker Chain Structure for a Series of Potent Topoisomerase Targeted Anticancer Drugs", J. Med., Chem, (2001), vol. 44, pp. 1407-1415.
Li et al., "The Syntheses of Cyclic Spermine Alkaloids: Analogues of Buchnerine and Budmunchiamine C", Helvetica Chimica Acta—vol. 86, 2003, pp. 310-323.
U.S. Appl. No. 12/529,101, filed Aug. 28, 2009, Dahmen et al.
U.S. Appl. No. 12/529,096, filed Aug. 28, 2009, Oftring et al.
U.S. Appl. No. 12/529,034, filed Aug. 28, 2009, Dahmen et al.
U.S. Appl. No. 12/529,072, filed Aug. 28, 2009, Dahmen et al.
U.S. Appl. No. 12/529,079, filed Aug. 28, 2009, Oftring et al.
U.S. Appl. No. 12/529,087, filed Aug. 28, 2009, Dahmen et al.
U.S. Appl. No. 12/529,107, filed Aug. 28, 2009, Oftring et al.
English translation of text of First Office Action from Chinese Patent Application No. 200880014267.9.
Masuzawa, Kuniyoshi et al., "Syntheses and Reactions of Nitrogen- and Sulfur-Analogs of 2- Piperazinone", Bulletin of the Chemical Society of Japan, vol. 41, pp. 702-707, 1968.

* cited by examiner

*Primary Examiner* — Nyeemah A Grazier
(74) *Attorney, Agent, or Firm* — Novak Druce Connolly Bove + Quigg LLP

(57) ABSTRACT

The invention relates to a process for preparing tetraethylenepentamine (TEPA) by hydrogenation of diethylenetriaminediacetonitrile (DETDN) over a catalyst. If appropriate, DETDN can also be present as a constituent of an amino nitrile mixture which additionally comprises diethylenetriaminemonoacetonitrile (DETMN).

19 Claims, No Drawings

METHOD FOR PRODUCING TETRAETHYLENEPENTAMINE

CROSS-REFERENCE TO RELATED APPLICATIONS

This application is a national stage application (under 35 U.S.C. §371) of PCT/EP2008/052335, filed Feb. 27, 2008, which claims benefit of European application 07103292.4, filed Mar. 1, 2007.

BACKGROUND OF THE INVENTION

The invention relates to a process for preparing tetraethylenepentamine (TEPA) by hydrogenation of diethylenetriaminediacetonitrile (DETDN) over a catalyst. If appropriate, DETDN can be present as a constituent of an amino nitrile mixture which additionally comprises diethylenetriaminemonoacetonitrile (DETMN).

It is generally known that aliphatic nitriles, which may be substituted by further functional groups, can be hydrogenated in the presence of catalysts to form the corresponding amines. As indicated below, such hydrogenation processes are also known for various amino nitriles for producing some amines. However, it has up to the present not been stated anywhere that TEPA can also be prepared from the amino nitrile DETDN or, if appropriate, from an amino nitrile mixture comprising DETDN and DETMN. The processes known hitherto for preparing TEPA are, however, as indicated below, associated with disadvantages.

Numerous processes for hydrogenating the α-amino nitrites aminoacetonitrile (AAN) and iminodiacetonitrile (IDAN) or β-amino nitrites have been described in the prior art. Thus, it is known that the hydrogenation of β-amino nitrites generally proceeds without problems, while the hydrogenation of α-amino nitrites is associated with the occurrence of numerous disadvantages such as hydrogenolysis of the C—CN bond or the $R_2N$—C bond. "Handbook of Heterogeneous Catalytic Hydrogenation for Organic Synthesis, pp. 213 to 215" indicates the problems of the hydrogenation of α-amino nitrites for the example of α-alkylamino nitriles or cyclic α-amino nitrites compared to β-amino nitrites. The known stability problems of α-amino nitrites are presumably the main reason why to the present day only the hydrogenation of the α-amino nitrites AAN or IDAN to EDA (ethylenediamine) or DETA (diethylenetriamine), respectively, has been described in detail. However, EDA or DETA are prepared industrially by means of the EDC or MEA process described below. However, a corresponding hydrogenation is not known for higher α-amino nitrites.

DE-A 3 003 729 describes a process for hydrogenating aliphatic nitriles, alkylene oxy nitrites and alkylene amino nitrites to primary amines of a cobalt or ruthenium catalyst in the presence of a solvent system. The solvent system used comprises water and ammonia together with an ether or polyether. The alkylene amino nitrites or alkylene oxy nitrites which can be used as starting materials are in each case defined by means of a complex general formula. As specific compounds or examples which can be hydrogenated to the corresponding diamine, mention is made of, inter alia, ethylenediaminedipropionitrile (EDDPN; also referred to as N,N'-bis(cyanoethyl)-ethylenediamine) or 3,3'-(ethylenedioxy) dipropionitrile. On the other hand, DE-A 3 003 729 does not make any reference to the use of individual compounds of DETA derivatives having cyanomethyl substituents, e.g. DETDN or DETMN. In addition, DETMN does not come within the general definition of alkylene amino nitrites according to this document.

EP-A 0 382 508 describes a process for the batchwise preparation of acyclic, aliphatic polyamines by hydrogenation of acyclic, aliphatic polynitriles in the liquid phase over Raney cobalt catalysts, preferably in the presence of anhydrous ammonia. Here, a polynitrile solution is fed into a reaction zone which comprises the Raney cobalt catalyst in an essentially oxygen-free atmosphere. During the entire time of the reaction, the polynitrile solution is fed in at a rate which is not greater than the maximum rate at which the polynitrile reacts with the hydrogen in the reaction zone. This process enables polyamines to be prepared from polynitriles such as iminodiacetonitrile (IDAN), nitrilotriacetonitrile, ethylenediaminetetralcetonitrile (EDTN) or further compounds which have 2 or more cyano groups and are not specified in more detail.

EP-A 212 986 relates to a further process in which the same aliphatic polynitriles as in EP-A 0 382 508 can be hydrogenated to the corresponding polyamines under a granular Raney cobalt catalyst in the presence of a liquid primary or secondary amine comprised in the feed stream. As amino components which have to be present, mention is made of, inter alia, ethylenediamine (EDA) and also numerous further primary or secondary amines.

EP-A 1 209 146 relates to a further process for the continuous hydrogenation of nitrites to primary amines, in which the respective nitrites are used in the liquid phase over a suspended, activated Raney catalyst based on an aluminum alloy and the reaction is carried out in the absence of ammonia and basic alkali metal or alkaline earth metal compounds. Nitriles which can be converted into the corresponding ethylene amines include, among many others, IDAN, EDTN, EDDPN or ethylenediaminemonopropionitrile (EDMPN).

EP-B 0 913 388 relates to a process for the catalytic hydrogenation of nitrites, which comprises contacting the nitrile with hydrogen in the presence of a cobalt sponge catalyst under conditions for carrying out the conversion of the nitrile groups into the primary amine. The cobalt sponge catalyst has been treated beforehand with a catalytic amount of lithium hydroxide and the process is carried out in the presence of water. Suitable nitrites are aliphatic nitriles having from 1 to 30 carbon atoms, including, inter alia, β-amino nitrites such as dimethylaminopropionitrile. A further process for preparing polyamines from the corresponding polynitriles is disclosed in DE-A 27 55 687. In this process, the hydrogenation is carried out over a pelletized hydrogenation catalyst in the presence of a stabilizer which inhibits decomposition of the catalyst. As polynitrile, it is possible to use, inter alia, ethylenediaminedipropionitrile (EDDPN). Suitable stabilizers include, inter alia, EDA.

US-A 2006/0041170 relates to a process for preparing triethylenetetramine (TETA), in particular TETA salts, and their use as drugs. In this multistage process, ethylenediaminediacetonitrite (EDDN) is prepared first. EDDN is subsequently derivatized on the nitrogen atoms of the two secondary amino groups by means of benzaldehyde or Boc protective groups (tert-butoxycarbonyl groups), for example to form a (cyclic) imidazolidine derivative. These derivatives are subsequently reduced, for example by reaction with hydrogen, to give the corresponding diamino compounds. These diamino compounds are in turn hydrolyzed in the presence of an acid to give the corresponding TETA salt. A disadvantage of this process is, in particular, that it is a multistage hydrogenation process in which the EDDN starting material used firstly has to be chemically derivatized in order to carry out the hydrogenation. A further disadvantage is that TETA is initially obtained as salt and not in the free base form.

There is therefore no report anywhere in the prior art that DETDN or amino nitrite mixtures comprising DETDN or DETMN can be used for preparing TEPA and, if appropriate, further ethylene amines. However, other processes for preparing TEPA are known.

EP-A 222 934 relates to a process for preparing higher alkylenepolyamines by reaction of a vicinal dihaloalkane with an excess of ammonia in the aqueous phase with addition of a strong base, resulting in formation of an imine intermediate which is subsequently reacted with an alkylenepolyamine to form the higher alkylenepolyamine. A suitable vicinal dihaloalkane is, in particular, ethylene dichloride (EDC or 1,2-dichloroethane). Alkylenepolyamines used are, in particular, ethylenediamine or higher ethylene amines such as DETA and also TEPA and triethylenetetramine (TETA). These processes (EDC processes) give a mixture of various ethylene amines (linear ethylene amines such as EDA, DETA, TETA, TEPA or higher ethylene amines and also cyclic derivatives such as piperazine (Pip), aminoethylpiperazine (AEPip) or higher piperazine derivatives such as diaminoethylpiperazine (DAEPip) or piperazineethylethylenediamine (PEEDA)). Depending on the ethylene amine added to the starting materials EDC and NH$_3$, the reaction mixture comprises a corresponding proportion of higher ethylene amines. If, for example, TEPA is to be specifically prepared, the ethylene amine TETA is added to the starting materials EDC and NH$_3$. As a result, the product (ethylene amine mixture) comprises a relatively high proportion of TEPA, but also the abovementioned further linear and cyclic ethylene amines. Disadvantages of this process are, in particular, that the process proceeds with low selectivity (giving an ethylene amine mixture) and that a specific ethylene amine (for example DETA) firstly has to be prepared and is subsequently introduced into the process to prepare the next higher ethylene amine (for example TETA) in a targeted manner or to increase the yield. However, this process represents a corrosion problem because of the starting materials used (haloalkanes) and the hydrochloric acid formed and also an environmental problem because of the salts formed.

DE-T 689 11 508 describes an alternative process for preparing linearly extended polyalkylenepolyamines such as TEPA. In this process, a bifunctional aliphatic alcohol is reacted with an amine reactant in the presence of a tungsten-comprising catalyst. A suitable bifunctional aliphatic alcohol is, in particular, monoethanolamine (MEA), an EDA or DETA, for example, can be used as amine reactants. This process in principle gives mixtures of linearly extended polyalkylenepolyamines (i.e. ethylene amine mixtures). These ethylene amine mixtures comprise DETA, TETA, TEPA, Pip or AEPip, with the proportion of the respective components varying according to the amine reactants used. If DETA is used as amine reactant, an ethylene amine mixture having a high proportion of TETA and TEPA is obtained. A disadvantage of this process is that the process proceeds with low selectivity (in respect of the components of the ethylene amine mixture obtained). A relatively large amount of by-products such as aminoethylethanolamine (AEEA) or higher hydroxy-comprising ethylene amines which are of little economic interest are formed here. The relatively large amounts of by-products obtained is due to MEA or the higher ethanolamines (e.g. AEEA) being able to react with themselves rather than with the amine used. Owing to the many (random) possible reactions, the selectivity to the linear TEPA is quite small and uncontrollable because of the coproducts. The synthesis can be carried out only at a partial conversion.

A review of the preparation of ethylene amines is given by the SRI report "CEH Product Review Ethyleneamines"; SRI International, 2003; pp. 1-53, in which EDA or DETA, in particular, are prepared by the above-described processes (using the starting materials EDC or MEA). Here, higher ethylene amines such as TETA or TEPA are formed as by-products or are obtained in relatively high yield by further reaction of the starting materials with EDA or DETA.

BRIEF SUMMARY OF THE INVENTION

It is therefore an object of the present invention to provide a simple and inexpensive process for preparing TEPA and, if appropriate, TETA.

This object is achieved by a process for preparing tetraethylenepentamine (TEPA), which comprises hydrogenating diethylenetriaminediacetonitrile (DETDN) in the presence of a catalyst and a solvent. If DETDN is present in an amino nitrile mixture comprising i) at least 30% by weight of DETDN and ii) at least 5% by weight of diethylenetriaminemonoacetonitrile (DETMN), TETA is obtained as further main product in addition to TEPA. For the purposes of the present invention, hydrogenation is reaction of DETDN or, if appropriate, further amino nitrites with hydrogen.

DETAILED DESCRIPTION OF THE INVENTION

The process of the invention has the advantage that TEPA and, if appropriate, the further main component TETA can be prepared with high conversion and/or selectivity. The increased selectivity is indicated, in particular, by both DETDN and, if appropriate, DETMN being able to be prepared selectively and the DETDN used being hydrogenated predominantly to TEPA. The by-products formed are mainly further linear and cyclic ethylene amines. The proportion of cyclic ethylene amines in the process of the invention is relatively small compared to the EDC process. However, some of the further ethylene amines are likewise interesting products of value (mainly the linear ethylene amines such as DETA) whose isolation is worthwhile, for example in the industrial processes.

DETDN and, if appropriate, DETMN are advantageously reacted completely or virtually completely. This is particularly important in industrial processes since unreacted starting material generally has to be recirculated to the product circuit or be disposed of. Processes in which relatively large amounts of DETDN or DETMN are not reacted are particularly disadvantageous because of the high instability of these amino nitrites. Firstly, both DETDN and DETMN tend to decompose at relatively high temperatures, so that the decomposition products cannot be recirculated to the respective circuit, and secondly this decomposition can also proceed with explosive vigor. Since the amino nitrites can be reacted completely in the process of the invention, no efforts have to be made to recirculate them to the production cycle.

A further advantage of the process of the invention is that, in contrast to the EDC process, the use of chlorinated hydrocarbons as starting material can be dispensed with. In addition, no hydrochloric acid or salts thereof is/are obtained as further reaction product. The disposal of the abovementioned substances is, particularly in the case of industrial processes, an (environmental) problem. An advantage compared to the MEA process is that the formation of AEEA and further compounds having a hydroxy function does not play a role because of the different starting materials.

In one embodiment of the process of the invention, DETDN is used as (main) starting material. In this embodiment, the content of further amino nitrites in the solution which is hydrogenated is preferably limited to ≦10% by weight, in particular ≦5% by weight, based on DETDN. In a further embodiment of the present invention, DETDN is present as a constituent of an amino nitrite mixture. The amino nitrile mixture comprises at least 30% by weight (percent by weight) of DETDN (component 1) together with at least 5% by weight of DETMN (component 2) and also, if appropriate, further amino nitrites. DETDN is normally comprised in the amino nitrite mixture in an amount of from 30 to 95% by weight, preferably from 30 to 70% by weight, particularly preferably from 30 to 50% by weight. The amino nitrite mixture normally comprises the component 2 in an amount of from 5 to 70% by weight, preferably from 30 to 70% by weight. It particularly preferably comprises 50-70% by weight of the component 2. The above percentages by weight of DETDN and DETMN and also the further amino nitrites are based on the total amount of amino nitrites comprised in the mixture. Water or other solvents which are additionally present are not taken into account in these amounts.

For the purposes of the present invention, the term "further amino nitrite" refers to any hydrocarbon-comprising compound which is different from DETON and DETMN and comprises at least three functional groups selected from among cyano groups, primary amino groups, secondary amino groups and tertiary amino groups, with the proviso that at least one cyano group and at least one secondary amino group are comprised in the hydrocarbon compound. Furthermore, aminoacetonitrile (MN) is also included among further amino nitrites.

Preferred further amino nitrites are selected from among iminodiacetonitrile (IDAN), ethylenediaminediacetonitrile (EDDN) and ethylenediaminemonoacetonitrile (EDMN).

While the further amino nitrites described above are compounds which are already known in the literature and processes for preparing these individual compounds are known to those skilled in the art, diethylenetriaminediacetonitrile (DETDN) and diethylenetriaminemonoacetonitrile (DETMN) are new compounds which have not previously been described in the literature. Accordingly, the amino nitrites DETDN and DETMN as such are also provided by the present invention. Likewise, a process for preparing DETDN or DETMN or a mixture thereof are also provided by the present invention.

DETDN can be prepared by reaction of DETA with hydrocyanic acid (HCN) and formaldehyde. The molar ratio of DETA to formaldehyde to HCN is preferably from 1:1.5:1.5 to 1:2:2 [mol/mol/mol]. As a result of the HCN, or if appropriate FACH (as described below), not being used in an excess over the amino groups of the starting materials, an improvement in the selectivity can be achieved in any hydrogenation which may subsequently be carried out.

DETDN is preferably prepared by reaction of diethylenetriamine (DETA) with formaldehyde cyanohydrin (FACH). The molar ratio of DETA to FACH is preferably from 1:1 to 1:2 [mol/mol]. The molar ratio of DETA to FACH is more preferably from 1:1.5 to 1:2 [mol/mol], in particular about 1:2 [mol/mol]. Methods of preparing DETA and FACH are known to those skilled in the art. In the process of the invention, DETA is preferably used in the form of its free base, but salts such as the dihydrochloride of DETA can also be used as starting material if appropriate.

FACH can be prepared by reaction of aqueous formaldehyde with hydrocyanic acid. Formaldehyde is preferably present as a 30-50% strength aqueous solution. Hydrocyanic acid is preferably used in a purity of from 90 to 100%. This reaction is preferably carried out at a pH of 5.5, which is preferably set by means of sodium hydroxide or ammonia. The reaction can be carried out at temperatures of from 20 to 70° C. in, for example, a loop reactor and/or tube reactor.

In place of purified hydrocyanic acid (HCN), crude HCN gas can also be chemisorbed in aqueous formaldehyde solution under the abovementioned conditions to form FACH. The crude HON gas is preferably produced by pyrolysis of formamide and comprises water and, in particular, small proportions of ammonia.

The aqueous FACH solution obtained can, if appropriate, be concentrated by vacuum evaporation under mild conditions, for example in a falling film evaporator or thin film evaporator. The FACH solution is preferably concentrated to a concentration of 50-80%. It is advantageous to stabilize the FACH solution by reducing the pH to ≦4, preferably ≦3, for example by addition of acid, for example by addition of phosphoric acid or preferably sulfuric acid, before carrying out the concentration.

As an alternative, DETDN can be prepared by reaction of a diethylenetriamine-formaldehyde adduct (DTFA) with hydrocyanic acid (HCN), with the molar ratio of DTFA to HCN preferably being from 1:1.5 to 1:2 [mol/mol]. Furthermore, DETA can also be reacted simultaneously (in parallel) with formaldehyde and hydrocyanic acid. It is also conceivable for a mixture of formaldehyde and hydrocyanic acid to be prepared first and subsequently be reacted with DETA. In these process alternatives, the molar ratio of DETA to the other starting material or materials is preferably from 1:1.5 to 1:2 [mol/mol].

The reaction can be carried out at from 10 to 90° C., preferably from 30 to 70° C., and at atmospheric pressure or under superatmospheric pressure. The reaction is preferably carried out in a tube reactor or a cascade of stirred vessels.

The preparation of DETDN is preferably carried out in a solvent, in particular in the presence of water. If appropriate, further water-miscible solvents can be used in addition to water. However, the presence of alcohols, in particular methanol, is less advantageous.

In the preparation of DETDN (main product), DETMN is obtained as important by-product in this embodiment of the process of the invention. Depending on the choice of the respective process parameters (for example starting material, temperature, solvent or pressure), the process of the invention can be controlled so that the proportion of DETDN in the reaction product varies and DETMN is obtained not as by-product but as second main reaction product. In this embodiment of the present invention, an amino nitrile mixture comprising DETDN together with DETMN (as main product) is thus prepared. Amino nitrile mixtures having the concentrations defined above are preferably prepared here.

An increase in the proportion of DETMN in the amino nitrile mixture is preferably achieved by using a relatively low molar proportion of FACH, formaldehyde or hydrocyanic acid within the abovementioned parameter ranges in the synthesis variants described above. Thus, for example, a molar ratio of DETA to FACH of from 1:1.5 to 1:1.8 [mol/mol] is used for increasing the proportion of DETMN. To prepare very pure DETMN, so that DETDN is present only as by-product, the molar proportion of FACH is reduced further, preferably to a ratio of DETA to FACH of about 1:1 [mol/mol].

Furthermore, in one embodiment of the present invention, an amino nitrile mixture comprising a relatively small proportion of DETMN, for example ≦10% by weight, preferably from 5 to 10% by weight, in particular ≦1% by weight, can be prepared by reaction of DETA with a very high molar proportion of FACH. Here, preference is given to using an aqueous solution of FACH having a concentration of ≧40% by weight or pure FACH. In this case, the molar ratio of DETA to FACH is preferably 1:2 [mol/mol].

After the preparation of DETDN or DETMN or mixtures comprising DETDN and DETMN, the individual compounds can be isolated by methods known to those skilled in the art. Preference is given to carrying out an isolation by crystallization. Crystallization processes as such are known to those skilled in the art. In one embodiment of the present invention, DETDN is preferably subjected to the hydrogenation directly after its preparation, generally without further purification steps. Here, DETDN is preferably present as constituent of one of the above-described amino nitrile mixtures which additionally comprise DETMN. If appropriate, one or more of the purification steps described below can be carried out before the hydrogenation. The hydrogenation is preferably carried out after the preparation of DETDN without additional intermediate steps with the exception of the removal of water and/or removal of low boilers.

i) Removal of Low Boilers

In an embodiment of the present invention, the low boilers are separated off from the reaction product from step a) before the hydrogenation. If FACH is used for preparing DETDN and, if appropriate, DETMN, the removal of low boilers can be carried out before the reaction of FACH with DETA.

Preference is given to separating off hydrocyanic acid (HCN) as low boiler. HON can also occur as decomposition product of FACH. Furthermore, any ammonia present can be separated off at this point. The removal is preferably effected by distillation, for example in the form of a Sambay distillation ("Chemie Ingenieur Technik, Vol. 27, pp. 257-261). If appropriate, the reaction mixture can also be stripped by means of nitrogen.

ii) Removal of Water

Water can be completely or partly removed either together with the low boilers or, preferably, after the removal of low boilers. The removal of the water is preferably carried out as a distillation. This can be carried out in one or more stages in an evaporator or a cascade of evaporators, with different pressures or temperatures being able to be set from stage to stage. The removal of water can also be carried out in a distillation column. The removal of water is preferably effected under reduced pressure. The amino nitrile or amino nitrile mixture which remains can still comprise residues of water and low boilers. Preference is given to a residual water content of at least 10% by weight. The low boilers are then comprised only in traces.

In general, any type/grade of DETDN and, if appropriate, of DETMN and of further amino nitrites can be used in the hydrogenation. The appropriate amino nitrites are preferably used in the form of their aqueous solution. As indicated above, DETDN and DETMN can be purified by methods known to those skilled in the art before use in the process of the invention. If DETDN is used in an amino nitrile mixture comprising DETDN or DETMN and, if appropriate, further amino nitrites in the process of the invention, the individual components of this amino nitrile mixture can be synthesized separately from one another or be combined in the appropriate amounts to form the amino nitrile mixture before use in the process of the invention.

DETDN is a solid at room temperature, as is DETMN. The hydrogenation of the process of the invention is consequently carried out in the presence of a solvent such as an organic solvent and/or water. Preference is given to using water as solvent, and mixtures of water and organic solvents such as ethers, in particular THF, can also be used if appropriate. The additional use of an organic solvent (i.e. an inert organic compound) in addition to water has been found to be advantageous since stabilization of the individual components of the aqueous amino nitrile mixture, in particular in the presence of the resulting amines, can be achieved in this way. In addition, a rinsing effect (reduction of rinsing cycles, reduction in the discharge of catalyst) on the catalyst used can be achieved by the use of organic solvents, as a result of which its operational life is increased or its consumption is reduced (longer catalyst life) and the space velocity over the catalyst can be improved.

A suitable solvent, which can comprise one or more components, should preferably have the following properties:
(a) the solvent should have a stabilizing effect on DETDN or, if appropriate, DETMN, in particular prevent its decomposition at the prevailing temperatures;
(b) the solvent should have a good solvent capability for hydrogen;
(c) the solvent should be inert under the reaction conditions;
(d) the reaction mixture (DETDN, if appropriate DETMN and water or organic solvent) should form a single phase under the reaction conditions;
(e) the solvent should be selected with a view to a preferred separation of the product from the product stream by distillation after the hydrogenation and separations which are energy-consuming or complicated in terms of apparatus (e.g. close-boiling mixtures or azeotropes which are difficult to separate) should be avoided.
(f) the solvent should be able to be readily separated from the products, i.e. the boiling point should be sufficiently different from those of the products. Here, a boiling point lower than those of the products is preferred.

Possible solvents (apart from water) are organic solvents, for example amides such as N-methylpyrrolidone (NMP) and dimethylformamide (DMF), aromatic and aliphatic hydrocarbons such as benzene and xylene, alcohols such as methanol, ethanol, propanol, isopropanol, butanol, isobutanol, secondary butanol and tertiary butanol, amines, esters such as methyl acetate or ethyl acetate and ethers such as diisopropyl ether, diisobutyl ether, glycol dimethyl ether, diglycol dimethyl ether, dioxane and tetrahydrofuran (THF). Ethers are preferably used in the process of the invention, more preferably cyclic ethers and particularly preferably tetrahydrofuran. In a further preferred embodiment, alcohols, in particular methanol, are used as organic solvent.

The organic solvent is used in a weight ratio to the amino nitrile used (DEDTN and, if appropriate, DETMN) of from 0.1:1 to 15:1. The concentration of the amino nitrite mixture in the solution in which the hydrogenation is carried out should be selected so that a suitable feed rate or residence time can be set. Preference is given to mixing amino nitrite in an amount of from 10 to 50% by weight with the solvent or mixture. Based on the particularly preferred solvents methanol and tetrahydrofuran, it is advantageous, for example, to use the amino nitrite in an amount of from 20 to 40% by weight based on the solvent.

If water is present, the proportion by weight of water in the solution is in the range from 0 to 60%, preferably from 10 to 30%. The amounts of water indicated are based on the amino nitrile/water mixture.

If appropriate, additional additives can be comprised in the solution in which the hydrogenation is carried out. Possible additives are principally hydroxides such as alkali metal hydroxides, alkoxides, amides, amines or if appropriate, ammonia. Preferred additives are amines, preferably the amine EDA, and ammonia, in particular EDA. Furthermore, acidic additives such as silicates can additionally be comprised in the solution. These substances can be added as pure substance or as a solution in a solvent. The process of the invention is preferably carried out with addition of additives.

As catalysts for the hydrogenation of the nitrile function to the amine, it is possible to use catalysts which comprise one or more elements of transition group 8 of the Periodic Table (Fe, Co, Ni, Ru, Rh, Pd, Os, Ir, Pt), preferably Fe, Co, Ni, Ru or Rh, particularly preferably Co or Ni, as active species. These include skeletal catalysts (also referred to as Raney® type; hereinafter also Raney catalyst) which are obtained by leaching (activation) of an alloy of hydrogenation-active metal and a further component (preferably Al). The catalysts can additionally comprise one or more promoters. In a preferred embodiment, Raney catalysts, preferably Raney cobalt or Raney nickel catalysts and particularly preferably Raney cobalt catalysts doped with at least one of the elements Cr, Ni or Fe or Raney nickel catalysts doped with one of the elements Mo, Cr or Fe, are used in the process of the invention.

The catalysts can be used as all-active catalysts or in supported form. Supports employed are preferably metal oxides such as $Al_2O_3$, $SiO_2$, $ZrO_2$, $TiO_2$, mixtures of metal oxides or carbon (activated carbons, carbon blacks, graphite).

The oxidic catalysts are activated by reduction of the metal oxides in a hydrogen-comprising gas stream at elevated temperature either outside the reactor or in the reactor before use. If the catalysts are reduced outside the reactor, this can be followed by passivation by means of an oxygen-comprising gas stream or embedding in an inert material in order to avoid uncontrolled oxidation in air and to make safe handling possible. As inert material, it is possible to use organic solvents such as alcohols or else water or an amine, preferably the reaction product. An exception in the activation is the skeletal catalysts which can be activated by leaching with aqueous base, as described in, for example, EP-A 1 209 146.

Depending on the process carried out (suspension hydrogenation, fluidized-bed process, fixed-bed hydrogenation), the catalysts are used as powder, crushed material or shaped bodies (preferably extrudates or pellets).

Particularly preferred fixed-bed catalysts are the all-active cobalt catalysts doped with Mn, P and alkali metal (Li, Na, K, Rb, Cs) which are disclosed in EP-A 742 045. The active catalyst composition of these catalysts before reduction with hydrogen comprises from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, in each case calculated as oxide.

Further suitable catalysts are the catalysts disclosed in EP-A 963 975, whose catalytically active composition before treatment with hydrogen comprises from 22 to 40% by weight of $ZrO_2$, from 1 to 30% by weight of oxygen-comprising compounds of copper, calculated as CuO, from 15 to 50% by weight of oxygen-comprising compounds of nickel, calculated as NiO, with the molar Ni:Cu ratio being greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ or $MnO_2$, and no oxygen-comprising compounds of molybdenum, for example the catalyst A disclosed in this document which has the composition 33% by weight of Zr, calculated as $ZrO_2$, 28% by weight of Ni, calculated as NiO, 11% by weight of Cu, calculated as CuO, and 28% by weight of Co, calculated as CoO.

Further suitable catalysts are those disclosed in EP-A 696 572, whose catalytically active composition before reduction with hydrogen comprises from 20 to 85% by weight of $ZrO_2$, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or manganese, calculated as $Al_2O_3$ or $MnO_2$; for example the catalyst specifically disclosed in this document which has the composition 31.5% by weight of $ZrO_2$, 50% by weight of NiO, 17% by weight of CuO and 1.5% by weight of MoOs. Further suitable catalysts are those described in WO-A-99/44984, which comprise (a) iron or a compound based on iron or mixtures thereof, (b) from 0.001 to 0.3% by weight, based on (a), of a promoter based on 2, 3, 4 or 5 elements selected from the group consisting of Al, Si, Zr, Ti, V, (c) from 0 to 0.3% by weight based on (a) of a compound based on an alkali metal and/or alkaline earth metal and (d) from 0.001 to 1% by weight based on (a) manganese.

Suspension processes are preferably carried out using Raney catalysts. In the case of Raney catalysts, the active catalyst is produced as "metal sponge" from a binary alloy (nickel, iron, cobalt with aluminum or silicon) by leaching out of one component by means of acid or alkali. Residues of the original alloying component often have a synergistic action.

The Raney catalysts used in the process of the invention are preferably produced from an alloy of cobalt or nickel, particularly preferably cobalt, and a further alloying component which is soluble in alkalis. Aluminum is preferably used as this soluble alloying component, but it is also possible to use other components such as zinc and silicon or mixtures of such components.

To activate the Raney catalyst, the soluble alloying component is completely or partly extracted with alkali, for which purpose it is possible to use, for example, aqueous sodium hydroxide. The catalyst can then be washed with, for example, water or organic solvents.

Individual or a plurality of further elements can be present as promoters in the catalyst. Examples of promoters are metals of transition groups IB, VIB and/or VIII of the Periodic Table, e.g. chromium, iron, molybdenum, nickel, copper, etc.

The activation of the catalysts by leaching of the soluble component (typically aluminum) can be carried out either in the reactor itself or before introduction into the reactor. The preactivated catalysts are air sensitive and pyrophoric and are therefore generally stored and handled under a medium such as water, an organic solvent or a substance which is present in the reaction according to the invention (solvent, starting material, product) or embedded in an organic compound which is solid at room temperature.

According to the invention, in a preferred embodiment, use is made of a skeletal Raney cobalt catalyst which has been obtained from a Co/Al alloy by leaching with aqueous alkali metal hydroxide solution, e.g. sodium hydroxide, and subsequent washing with water and preferably comprises at least one of the elements Fe, Ni, Cr as promoters.

Such catalysts typically comprise cobalt together with 1-30% by weight of Al, particularly preferably 2-12% by weight of Al, very particularly preferably 3-6% by weight of Al, 0-10% by weight of Cr, particularly preferably 0.1-7% by weight of Cr, very particularly preferably 0.5-5% by weight of Cr, in particular 1-3.5% by weight of Cr, 0-10% by weight of Fe, particularly preferably 0.1-3% by weight of Fe, very particularly preferably 0.2-1% by weight of Fe, and/or 0-10% by weight of Ni, particularly preferably 0.1-7% by weight of Ni, very particularly preferably 0.5-5% by weight of Ni, in particular 1-4% by weight of Ni, with the percentages by weight in each case being based on the total weight of the catalyst.

As catalyst in the process of the invention, use can advantageously be made of, for example, a skeletal cobalt catalyst "Raney 2724" from W.R. Grace & Co. This catalyst has the following composition:

Al: 2-6% by weight, Co: $\geqq$86% by weight, Fe: 0-1% by weight, Ni: 1-4% by weight, Cr: 1.5-3.5% by weight.

It is likewise possible to use a skeletal nickel catalyst which has been obtained from an Ni/Al alloy by leaching with aqueous alkali metal hydroxide solution, e.g. sodium hydroxide, and subsequent washing with water and preferably comprises at least one of the elements Fe, Cr as promoters for the purposes of the invention.

Such catalysts typically comprise nickel together with 1-30% by weight of Al, particularly preferably 2-20% by weight of Al, very particularly preferably 5-14% by weight of Al, 0-10% by weight of Cr, particularly preferably 0.1-7% by weight of Cr, very particularly preferably 1-4% by weight of Cr, and/or 0-10% by weight of Fe, particularly preferably 0.1-7% by weight of Fe, very particularly preferably 1-4% by weight of Fe, with the percentages by weight in each case being based on the total weight of the catalyst.

As catalyst in the process of the invention, use can advantageously be made of, for example, a skeletal nickel catalyst A 4000 from Johnson Matthey.

This catalyst has the following composition

Al: $\leqq$14% by weight, Ni: $\geqq$80% by weight, Fe: 1-4% by weight, Cr: 1-4% by weight.

In the case of decreasing activity and/or selectivity of the catalysts, they can be regenerated by methods known to those skilled in the art, as disclosed, for example, in WO 99/33561 and the documents cited therein.

The regeneration of the catalyst can be carried out in the actual reactor (in situ) or on the catalyst which has been removed from the reactor (ex situ). In the case of fixed-bed processes, regeneration is preferably carried out in situ; in the case of suspension processes, part of the catalyst is preferably taken continuously or discontinuously from the reactor, regenerated ex situ and returned.

The temperatures at which the process of the invention is carried out are in the range from 40 to 150° C., preferably from 70 to 140° C., in particular from 80 to 130° C.

The pressure prevailing in the hydrogenation is generally in the range from 5 to 300 bar, preferably from 30 to 250 bar, particularly preferably from 40 to 160 bar.

In a preferred embodiment, DETDN or the amino nitrile mixture comprising DETDN and DETMN is fed to the hydrogenation at a rate which is not greater than the rate at which the DETDN and, if applicable, the other components of the amino nitrile mixture react with hydrogen in the hydrogenation.

The feed rate is preferably set so that effectively quantitative conversion is achieved. This is influenced by temperature, pressure, type of mixture, amount and type of catalyst, the reaction medium, quality of mixing of the contents of the reactor, residence time, etc.

The process of the invention is carried out using a solvent (or a plurality of solvents) which is firstly mixed completely with DETDN or the amino nitrile mixture. The solution obtained, which may, if appropriate, also comprise additives, is subsequently fed into the reaction vessel comprising the catalyst. If appropriate, for example in semibatch processes, part of the solvent can initially be placed in the reaction vessel together with the catalyst, whereupon the solution is introduced. In the case of continuous processes, a partial amount of the solvent can also be introduced into the reaction vessel separately from the solution, the DETDN, the solvent and, if appropriate, the additive. If appropriate, for example in semibatch processes, part of the solvent can initially be placed in the reaction vessel together with the catalyst, whereupon the solution is introduced. Particular preference is given to the amino nitrile being fed in aqueous solution and the organic solvent being introduced separately.

The process of the invention for preparing TEPA by hydrogenation of DETDN can be carried out continuously, semi-continuously or batchwise in a fixed-bed, fluidized-bed or suspension mode in customary reaction vessels which are suitable for catalysis. Reaction vessels in which contacting of the amino nitrile and the catalyst with the gaseous hydrogen under pressure is possible are suitable for carrying out the hydrogenation.

The hydrogenation in the suspension mode can be carried out in a stirred reactor, jet loop reactor, jet nozzle reactor, bubble column reactor or in a cascade of identical or different reactors of these types. In the case of hydrogenation over a fixed-bed catalyst, tube reactors but also shell-and-tube reactors are conceivable.

In the case of a fixed-bed catalyst, the amino nitrile is conveyed through the catalyst bed in an upward or downward direction. However, the suspension mode is preferably used in semibatch and preferably continuous operation.

The hydrogenation of the nitrile groups takes place with liberation of heat which generally has to be removed. Heat removal can be effected by means of built-in heat-exchange surfaces, cooling jackets or external heat exchangers in a circuit around the reactor. The hydrogenation reactor or a hydrogenation reactor cascade can be operated in a single pass. As an alternative, a recycle mode of operation in which part of the output from the reactor is recirculated to the reactor inlet, preferably without prior work-up of the recycle stream, is also possible. This enables optimum dilution of the reaction solution to be achieved. In particular, the recycle stream can be cooled in a simple and inexpensive manner by means of an external heat exchanger and the heat of reaction can thus be removed. The reactor can also be operated adiabatically, with the increase in the temperature of the reaction solution being able to be limited by means of the cooled recycle stream. Since the reactor itself then does not have to be cooled, a simple and inexpensive construction is possible. An alternative is a cooled shell-and-tube reactor (only in the case of the fixed bed). A combination of the two modes of operation is also conceivable. Here, a fixed-bed reactor is preferably installed downstream of a suspension reactor.

The process of the invention gives TEPA as main product (1st case) and further ethylene amines as secondary components as a result of the hydrogenation. If an amino nitrile mixture comprising DETDN and DETMN is used in the process of the invention, an ethylene amine mixture comprising TEPA and TETA as main components (2nd case) and further ethylene amines as secondary components is obtained. The process of the invention is illustrated for the second case in scheme 1 below, in which an amino nitrile mixture comprising DETDN and DETMN is prepared jointly and is subsequently hydrogenated.

Scheme 1

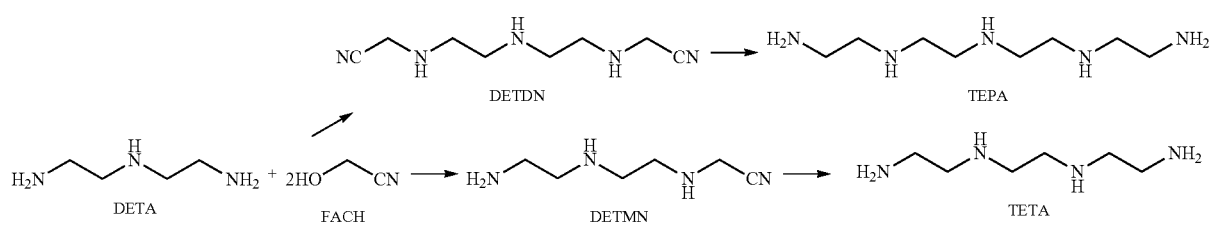

In the second case, the term "ethylene amine mixture" is used because the reaction product comprises two main components (TEPA and TETA), while in the first case only one main product (TEPA) is present. The by-products indicated below are consequently not taken into account in the definition of turns in these two cases.

In the first case, TEPA is obtained in a selectivity of preferably ≧75% by weight, in particular ≧90% by weight, based on the amount of DETDN used.

For the purposes of the present invention, the term "further ethylene amine" refers to any hydrocarbon-comprising compound which is different from TEPA (1st case) and from TETA and TEPA (2nd case) and comprises at least two ethylene units and at least two functional groups selected from among primary amino groups, secondary amino groups and tertiary amino groups. For the purposes of the present invention, cyclic compounds such as piperazine (Pip) and its derivatives are also encompassed by the term further ethylene amine. Likewise, ethylenediamine (EDA) should be regarded as a further ethylene amine. DETA and Pip are also named as $C_4$-(by-) products and AEPip and TETA as $C_6$-(by)-products.

Preferred further ethylene amines are selected from among TETA (only in the 1st case) and diethylenetriamine (DETA), piperazine (Pip), aminoethylenepiperazine (AE-Pip) and diaminoethylpiperazine (DAEPip) and also piperazinylethylethylenediamine (PEEDA).

After the hydrogenation, the product obtained (TEPA or ethylene amine mixture) can be purified further if appropriate, for example by separating off the solvent and/or the catalyst by methods known to those skilled in the art. In particular, the main products (TEPA and, if appropriate, TETA) can be isolated together or individually from the reaction product by methods known to those skilled in the art. If the two main products are isolated together, for example by distillation, they can subsequently be separated into the two individual products. Pure TEPA and pure TETA are thus ultimately obtained. Other impurities, by-products or further ethylene amines such as DETA or Pip can likewise be separated off from the respective product by methods known to those skilled in the art. As an alternative, a joint isolation of TETA with the cyclic products PEEDA or DEAPip can also be carried out.

In a preferred embodiment, the process of the invention is carried out using tetrahydrofuran or methanol as solvent. The temperature in the hydrogenation is preferably from 80 to 140° C., and the pressure is preferably from 40 to 160 bar. The hydrogenation is preferably carried out in the presence of EDA and/or, if appropriate, ammonia.

The following examples illustrate the process of the invention. The proportions are given in % by weight unless indicated otherwise. An internal standard, diethylene glycol dimethyl ether (DEGDME), conveyed with the reaction mixture allows quantification of the product by determination of any volatile decomposition products formed. Quantification is effected by means of gas chromatography (GC), with methanol being in each case added to the samples taken in order to homogenize them.

EXAMPLES

General Method for the Synthesis of Form Aldehyde Cyanohydrin (FACH)

Variant a)

6000 g (60 mol) of formaldehyde (30%) are placed in a 6 l reaction vessel provided with a propeller stirrer and a pH of 5.5 is set by means of sodium hydroxide solution (1 mol/l). 1661 g (61.2 mol) of hydrocyanic acid are introduced in gaseous form via a heated U-tube below the stirrer over a period of 2.5 hours, with the reaction temperature being maintained at 30° C. and the pH being maintained at 5.5. After stirring for a further 30 minutes, the pH is brought to 2.5 by means of sulfuric acid (50% strength). The corresponding content is determined by Liebig titration.

Variant b)

7000 g (70 mol) of formaldehyde (30%) are placed in a 6 l reaction vessel provided with a propeller stirrer and a pH of 5.5 is set by means of sodium hydroxide solution (1 mol/l). 1938 g (71.4 mol) of hydrocyanic acid are introduced in gaseous form via a U-tube heated to 50° C. below the stirrer over a period of 3 hours, with the reaction temperature being maintained at 30° C. and the pH being maintained at 5.5. After stirring for a further 10 minutes, the pH is brought to 2.5 by means of sulfuric acid (50% strength). To separate off low boilers, in particular hydrocyanic acid, the output from the reaction is subjected to a Sambay distillation (as described in "Chemie Ingenieur Technik, Vol. 27, pp. 257-261) (1 mbar, 30° C.). The corresponding content is determined by Liebig titration and a content of 43-44% or 67% of FACH is set if appropriate by addition of water.

Example 1

Formaldehyde Cyanohydrin

FACH is prepared by variant b) of the general method.
Diethylenetriaminediacetonitrile 165 g (2.2 mol) of EDA are placed in a 2 l reaction vessel and 511 g (4 mol) of FACH (44.6%) are added dropwise over a period of 2 hours at a temperature of not more than 30° C. while cooling in ice. After stirring for a further 3 hours, the slightly yellowish solution is dispensed. The conversion of FACH is 99.3% according to Liebig titration. The reaction mixture comprises 0.09% of free hydrocyanic acid (determined by Volhard titration). Titration indicates a DETDN yield of 90.2% based on FACH used. DETDN cannot be determined by titration. Assuming that DETMN is formed from reacted diethylenetriamine which does not react to form DETDN, the total amino nitrile yield is 93.5% and the yield of DETMN is thus 3%.

Tetraethylenepentaamine (TEPA)

a) The material obtained (DETDN-production) is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture of 13.8 g of the crude EDDN solution, 13.8 g of an internal standard and 10 g of water in 106 g of THF is fed in over a period of 120 minutes. The reaction mixture is stirred under the reaction conditions for a further 60 minutes. The product mixture is homogenized by means of methanol. The selectivity to PEEDA is 12% and that to TEPA is 67%. In addition, 9% of $C_4$ and $C_6$ products (Pip, DETA, TGTA and AEPip) are obtained.

The excess of DETA in the DETDN synthesis results in formation of DETMN which is hydrogenated to the $C_6$-products TETA and AEPip.

b) The material obtained (DETDN-production) is hydrogenated in a semibatch process. Here, 3.25 g of a Cr-doped Raney cobalt catalyst and also 15 ml of THF and 13.5 g of EDA are placed in a 270 ml autoclave. The autoclave is heated to 120° C. and pressurized with hydrogen to a total pressure of 100 bar. A mixture of 13.8 g of the crude EDDN solution, 13.8 g of an internal standard and 10 g of water in 106 g of THF is fed in over a period of 120 minutes. The reaction mixture is stirred under the reaction conditions for a further 60 minutes. The product mixture is homogenized by means of methanol. The selectivity to PEEDA is 6% and that to TEPA is 76%. In addition, 14% by weight of $C_4$ and $C_6$-products are obtained.

The addition of EDA results in formation of more linear TEPA. There is likewise an increase in $C_4$ and $C_6$-products due to EDA condensation.

c) The material obtained (DETDN-production) is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture of 13.8 g of the crude DETDN solution, 13.8 g of an internal standard in 106 g of THF is fed in over a period of 120 minutes. The reaction mixture is stirred under the reaction conditions for a further 60 minutes. The product mixture is homogenized by means of methanol. The selectivity to PEEDA is 6% and that to TEPA is 82%. In addition, 10% of $C_4$- and $C_6$-products are obtained.

Compared to example 1a and 1b, an additional addition of water is omitted, which has a positive effect on TEPA-selectivity.

The invention claimed is:

1. A process for preparing tetraethylenepentamine (TEPA) which comprises hydrogenating diethylenetriaminediacetonitrile (DETDN) in the presence of a catalyst and a solvent.

2. The process according to claim 1, wherein DETDN is present in an amino nitrile mixture comprising i) at least 30% by weight of DETDN and ii) at least 5% by weight of diethylenetriaminemonoacetonitrile (DETMN).

3. The process according to claim 1, wherein a Raney catalyst is used.

4. The process according to claim 3, wherein a skeletal Raney cobalt catalyst which has been obtained from a Co/Al alloy by leaching with aqueous alkali metal hydroxide solution and comprises at least one of the elements Fe, Ni or Cr as promoter is used.

5. The process according to claim 1, wherein the solvent is water or an organic solvent.

6. The process according to claim 5, wherein the organic solvent is tetrahydrofuran or methanol.

7. The process according to claim 1, wherein the pressure is from 30 to 250 bar or the temperature is from 70° C. to 140° C.

8. The process according to claim 2, wherein the amino nitrile mixture comprises from 10 to 70% by weight of DETMN.

9. The process according to claim 1, wherein TEPA, triethylenetetramine (TETA) and optionally further ethylene amines which are comprised as by-products in the reaction product obtained in each case are isolated after the hydrogenation.

10. The process according to claim 2, wherein DETDN and DETMN are prepared by reaction of diethylenetriamine (DETA) and formaldehyde cyanohydrin (FACH).

11. The process according to claim 10, wherein the reaction of DETA and FACH is carried out in the presence of water.

12. The process according to claim 10, wherein the hydrogenation of DETDN is carried out directly after the preparation of DETDN from DETA and FACH, with removal of water or removal of low boilers being carried out optionally before the hydrogenation.

13. The process according to claim 12, wherein DETDN is present in an amino nitrile mixture comprising i) at least 30% by weight of DETDN and ii) at least 5% by weight of diethylenetriaminemonoacetonitrile (DETMN).

14. The process according to claim 1, wherein the DETDN is fed to the hydrogenation at a rate which is not greater than the rate at which DETDN reacts with hydrogen in the hydrogenation.

15. The process according to claim 1, wherein the hydrogenation is carried out in the presence of an additive.

16. The process according to claim 15, wherein the hydrogenation is carried out in the presence of ethylenediamine (EDA) or ammonia.

17. A process for preparing an amino nitrile selected from among diethylenetriaminediacetonitrile (DETDN) and diethylenetriaminemonoacetonitrile (DETMN) a mixture thereof, which comprises reacting diethylenetriamine (DETA) with formaldehyde and hydrocyanic acid (HCN).

18. The process according to claim 17, wherein formaldehyde and HCN are firstly reacted to form formaldehyde cyanohydrin (FACH) and DETA subsequently reacted with FACH.

19. The process according to claim 18, wherein the molar ratio of DETA to FACH is from 1:1.5 to 1:2.

* * * * *